United States Patent [19]

Marlow et al.

[11] Patent Number: 5,618,303
[45] Date of Patent: *Apr. 8, 1997

[54] ENDOSCOPIC INSTRUMENT SYSTEM AND METHOD

[75] Inventors: Scott C. Marlow, Chesterland; Haans K. Petruschke, Kirtland; Donald B. Coon, Chesterland; John T. Nelson, Kirtland, all of Ohio

[73] Assignee: Marlow Surgical Technologies, Inc., Willoughby, Ohio

[ * ] Notice: The term of this patent shall not extend beyond the expiration date of Pat. No. 5,368,606.

[21] Appl. No.: 125,926

[22] Filed: Sep. 23, 1993

Related U.S. Application Data

[63] Continuation-in-part of Ser. No. 907,853, Jul. 2, 1992, Pat. No. 5,368,606.

[51] Int. Cl.$^6$ .................................... A61B 17/00
[52] U.S. Cl. .......................... 606/205; 606/170; 606/174; 128/751
[58] Field of Search ............................... 606/51, 52, 174, 606/205–210; 128/750–755; 604/22

[56] References Cited

U.S. PATENT DOCUMENTS

| | | | |
|---|---|---|---|
| 4,569,131 | 2/1986 | Falk et al. | 128/751 |
| 4,977,900 | 12/1990 | Fehling et al. | 128/751 |
| 5,147,357 | 9/1992 | Rose et al. | 606/52 |
| 5,366,477 | 11/1994 | LeMarie, III et al. | 606/208 |

OTHER PUBLICATIONS

Medicon Instrument Catalogue, pp. 440, 441, 443, 451, 585, 686, copyright 1986.
V. Mueller, The Surgical Armamentarium, Baxter Healthcare Corporation copyright 1988, pp. F176–F177.

*Primary Examiner*—Michael Buiz
*Assistant Examiner*—William Lewis
*Attorney, Agent, or Firm*—Thompson Hine & Flory LLP

[57] ABSTRACT

An endoscopic instrument system which includes a handle portion with a scissors grip, a shaft extending from the scissors grip and shaped to extend through a cannula, and a plurality of disposable end tools, each mountable on and removable from the end of the shaft by hand without tools and actuatable by the scissors handle. In a preferred embodiment, the scissors handle actuates a rod extending through the shaft which is connected to the end tool. The end tool includes a pair of jaws pivotally mounted on the support and connected to a reciprocating stub shaft by links. The stub shaft is connected to the actuating rod of the handle portion so that movement of the scissors handle causes the jaws to pivot relative to each other. The end tool may take the form of a scissor, grasper, biopsy or dissector, depending upon the specific shape of the jaws. An advantage of the invention is that the support of the end tools is made of a relatively inexpensive plastic material such that the end tools may be discarded when the jaws become dull, thus obviating the need for repeated cleaning and sharpening and eliminating the most difficult portion to clean.

32 Claims, 2 Drawing Sheets

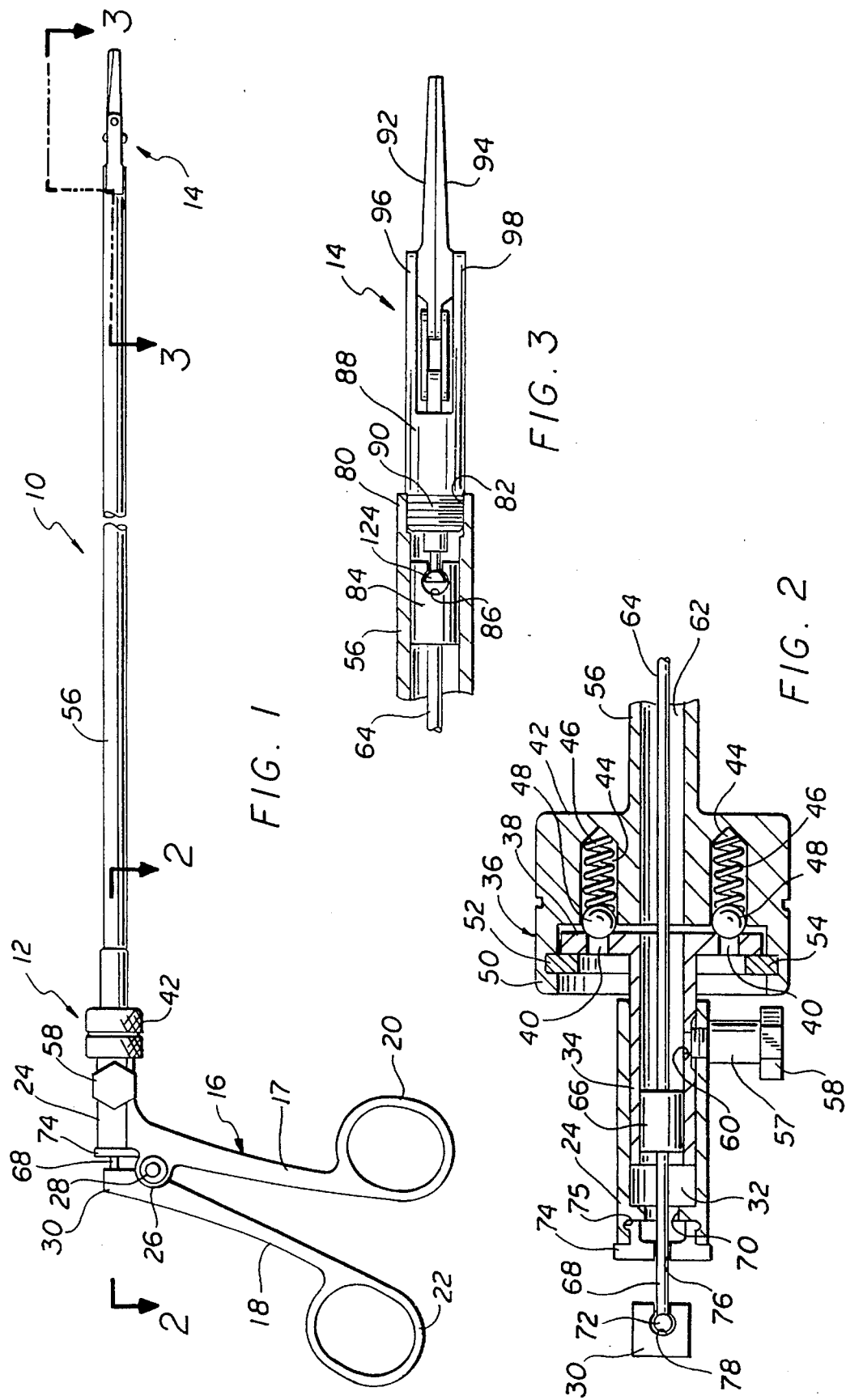

ENDOSCOPIC INSTRUMENT SYSTEM AND METHOD

CROSS-REFERENCE TO RELATED APPLICATION

This application is a continuation-in-part of Ser. No. 07/907,853 filed Jul. 2, 1992, now U.S. Pat. No. 5,368,606.

BACKGROUND OF THE INVENTION

The present invention relates to surgical instruments and more particularly, to endoscopic instruments suitable for use with a trocar or cannula.

A branch of endoscopic surgery is laparoscopic surgery which involves the use of a cannula that is inserted through an incision in the skin of the subject to provide access to an internal cavity, such as the thoracic cavity. An example of such a cannula is disclosed in Hasson U.S. Pat. No. 5,002,557, the disclosure of which is incorporated herein by reference. Surgery is performed with a laparoscopic instrument, which typically includes a scissors handle and an elongate shaft terminating in a pair of pivoting jaws. The handle includes a scissors or pliers grip which, when squeezed and released, reciprocates a rod extending through the shaft to pivot the jaws. The jaws and shaft are sized to be inserted through the cannula into the body cavity where the surgery is to be performed. Similar devices are employed in thoroscopic and arthroscopic surgery.

As with any surgical instruments, should the tool include sharpened jaws for cutting, it is desirable to maintain the sharpened edges as sharp as possible for each operation. Further, it is also desirable to design the instrument so that it can be easily and thoroughly cleaned after each operation. However, a disadvantage with unitary instruments—that is, instruments in which the handle, shaft and cutting tool are permanently attached to each other—is that cleaning of the instrument and sharpening of the tool after each operation becomes time-consuming and costly.

Accordingly, attempts have been made to provide laparoscopy instruments which minimize the time and expense of cleaning and sharpening. For example, some laparoscopy instruments are made in which substantially the entire instrument is constructed of plastic, except for the shaft rod and jaws, so that the entire instrument is disposable after each operation. Alternately, instruments such as those disclosed in Falk et al. U.S. Pat. No. 4,569,131 are designed in which the handle is separable from the shaft and jaws, so that the unitary shaft, jaws and rod may be disposed after each use, or cleaned and sharped separately from the handle. A disadvantage with these types of designs is that the disposable component—whether it be the entire instrument or only the shaft and cutting tool—provides an undesirably high volume of medical waste which requires special disposal procedures. Further, disposable instruments made largely of plastic are somewhat flimsy and difficult to maneuver.

Accordingly, there is a need for a laparoscopy instrument which eliminates the need for repeated sharpening of the cutting surfaces of the instrument, facilitates cleaning and reduces cross-contamination potential.

SUMMARY OF THE INVENTION

The present invention is an endoscopic instrument system which includes a handle portion having an elongate shaft for insertion through a cannula and an end tool which is attachable to and removable from the end of the shaft by hand. In the preferred embodiment, a plurality of end tools are provided, each of the end tools having pivoting jaws which actually contact the tissue of the subject during an operation. The end tools preferably include plastic components which lower their unit cost, and are disposable subsequent to use. One advantage of the present invention is that the disposable component of the entire instrument system is relatively small, thereby minimizing the cost of using the instrument over several operations and minimizing the volume of medical waste comprised by the disposable components of the instrument.

In a preferred embodiment, the handle portion includes pivoting scissor handles and an actuating rod which extends through the shaft. The rod terminates in a clevis which receives the enlarged tip of a stub shaft that is reciprocatably mounted within the end tool. The stub shaft is connected to a pair of pivoting jaws by links so that reciprocal movement of the stub shaft causes the jaws to pivot relative to the end tool in a scissors fashion.

The end tool includes a support which is made of a glass fiber reinforced plastic and threads onto the open end of the handle shaft. The pivoting jaws of the end tools may be formed to perform a variety of tasks; for example, the jaws can be in the form of scissors, graspers, biopsy, or dissectors.

Another advantage of the present invention is that only the portions of the instrument which become most contaminated during an operation and are most difficult to clean—namely, the jaws and linkage operating the jaws—are disposed of with the end tool. In the preferred embodiment, a cleaning port extends through the handle portion and facilitates the flushing of the shaft with an appropriate liquid cleaning agent after each operation. A direct result of incorporating the laparoscopy instrument of the present invention in a hospital operating room procedure is that a relatively few handle portions need to be present while having a relatively large number of end tools, in contrast to prior procedures in which an extensive array of unitary instruments must be present. Consequently, a tip can be attached to the handle shaft by hand, without tools, immediately prior to an operation. After the operation is completed, the used tip can be unthreaded from the shaft end, the stub shaft separated from the rod by disengagement of the hemispherical tip from the clevis, and the tip discarded, again by hand without need of tools or other devices. Further, each surgeon may be provided with a set of end tools, each performing a different function, and each selected from an array of end tools to suit a particular surgeon's needs and preferences.

Accordingly, it is an object of the present invention to provide an endoscopic instrument system which eliminates the need for repeatedly sharpening the cutting jaws of the instrument; an instrument system in which the linkage components which are the most difficult to clean are disposable, thereby obviating the necessity for repeated cleaning; an instrument system in which the shaft portion is easily cleaned after each operation; an instrument system in which the cutting surfaces and linkages are disposable such that the volume of disposed equipment is minimized; and instrument system having a disposable cutting element in which the support component is made of a relatively inexpensive plastic material; an instrument system having a plurality of attachable end tools which can be customized for a particular practitioner or application; an instrument system comprising a handle, shaft and removable tip in which the tip can be attached and removed by hand, without tools, in the field; and an instrument system which is relatively easy to manufacture and utilize.

Other objects and advantages of the present invention will be apparent from the following description, the accompanying drawing and the appended claims.

BRIEF DESCRIPTION OF THE DRAWINGS

FIG. 1 is a side elevation of the handle portion and one end tool of a preferred embodiment of the endoscopic instrument system of the present invention;

FIG. 2 is a section taken at line 2—2 of FIG. 1;

FIG. 3 is a section taken at line 3—3 of FIG. 1;

DETAILED DESCRIPTION

Figure 4:
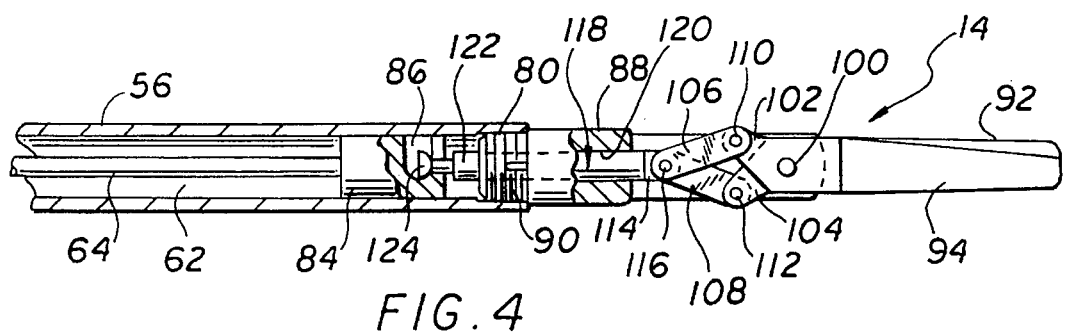
FIG. 4 is a detail of the instrument of FIG. 1 showing the shaft end in section and a portion of the end tool broken away.

As shown in FIG. 1, the endoscopic instrument system of the present invention, generally designated 10, includes a handle portion, generally designated 12, and an end tool, generally designated 14. The handle portion 12 includes a scissors component 16 which is gripped by the user and has front and rear scissors handles 17, 18, respectively. Scissors handles 17 and 18 include finger loops 20, 22.

Scissors handle 17 is attached to a cylindrical housing 24 and includes a clevis 26 which is engaged by scissors handle 18 and secured by a screw 28. When scissor handle 18 is pivoted relative to handle 17 about screw 28, the upper end 30 of handle 18 reciprocates relative to the housing 24.

As shown in FIG. 2, the housing 24 includes a hollow interior 32 which receives an inner sleeve 34 of a rotatable coupling 36. The inner sleeve 34 includes a flange 38 having a plurality of orifices 40 spaced about its periphery. The coupling 36 includes a coupling body 42 having a plurality of cylindrical cavities 44, each receiving an extension spring 46 which urges a ball 48 against an adjacent one of the orifices 40. The balls 48 are larger in diameter than the orifices so that the orifices merely provide seats for the balls 48. The inner end 50 of the coupling body 36 includes an annular groove 52 which receives a split ring 54. The split ring 54 retains the coupling body 42 on the flange 38. The body 42 is unitary with a hollow, elongate shaft 56 (see also FIG. 1). While the shaft 56 of the preferred embodiment is made of surgical stainless steel, it is within the scope of the invention to provide a flexible shaft of plastic material or a bowden cable.

The external surface of the body 42 is knurled to facilitate grasping by a user. The coupling 36 enables the shaft 56 to be rotated relative to the housing 24 of the handle portion 12, and the engagement of ball 48 and orifices 40 provide detent stops.

The housing portion 24 includes a lateral tube 57 which is capped by a removable nut 58 and communicates with the interior 32 of the housing. The tube 57 extends through an opening 60 in the sleeve 34 to communicate with the interior 62 of the coupling 36 and shaft 56.

The handle portion 12 includes a rod 64 which extends through the interiors 62, 32 of the shaft 56 and housing 24, respectively. The rod includes an enlarged, cylindrical segment 66 which engages the interior or internal wall of the sleeve 34 for location purposes and a rear segment 68 which protrudes through an end opening 70 in the housing 24 to terminate in a spherical end 72. The housing 24 includes a plastic end cap 74 mounted in a dovetail slot 75 which provides a seal about the extension 68. The extension 68 passes through an orifice 76 in the cap and the end 72 of the extension is received within a clevis 78 formed in the upper end 30 of the handle 18. Consequently, pivoting movement of the handle 18 relative to handle 17 causes the upper end 30 to reciprocate relative to the housing 24, reciprocating the rod 64 relative to the handle portion 12.

As shown in FIG. 3, the outer end 80 of the shaft 56 includes a threaded interior surface 82. The end 84 of the rod 64 includes a clevis 86. The end tool 14 includes a support 88, preferably made of a glass-filled plastic, such as 40% glass-filled polyetherimide. Other plastics include polyethersulfone and polyetheretherketone. Support 88 has a threaded inner end 90 which is shaped to thread into the threaded interior 82 of the end 80 of shaft 56. The support 88 mounts a pair of jaws 92, 94, which are best shown in FIG. 4.

The support 88 includes a pair of arms 96, 98 (see FIG. 3) which receive a rivet 100 that mounts the jaws 92, 94 for pivotal movement relative to the support and to each other. The jaws 92, 94 each include ears 102, 104 which are pivotally attached to links 106, 108 by rivets 110, 112. The links 106, 108 are, in turn, pivotally attached to a knuckle 114 by a rivet 116. The knuckle 114 forms a portion of a stub shaft 118 which is slidably mounted within a passage 120 formed in the support 88. The stub shaft is sized such that an inner end 122 protrudes rearwardly from the threaded end 90 and terminates in a hemispherical tip 124 which is shaped to be seated within the clevis 86.

Figure 5:
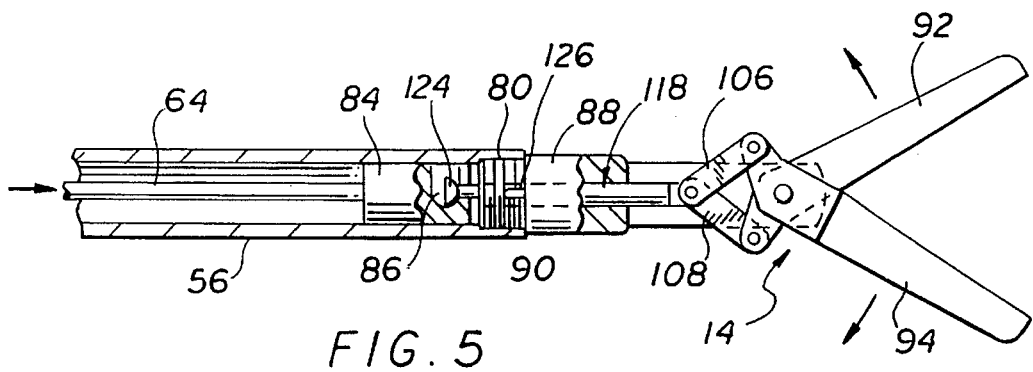
FIG. 5 is the detail of FIG. 4 in which the tool jaws have been pivoted to an open position.

As shown in FIG. 5, displacement of the rod 64 relative to the shaft 56 by pivoting the handles 17, 18 in the manner previously described causes the end 84 of the rod to displace the stub shaft 118 outwardly relative to the support 88. This outward displacement causes the links 106, 108 to pivot the jaws 92, 94 outwardly away from each other. Conversely, displacement of the rod 64 inwardly, caused by squeezing the handles 17, 18 together (see FIG. 1), causes the stub shaft 118 to be displaced inwardly relative to the support 88, so that the links 106, 108 draw the jaws 92, 94 together. Consequently, pivotal movement of handle 18 relative to handle 17 causes the jaws 92, 94 to pivot relative to each other.

To remove the end tool 14 from the shaft 56, the support 88 is first threaded out of the threaded end 80 of the shaft 56. The loops 20, 22 of the handles 17, 18 are drawn together, which displaces the rod end 84 outwardly from the shaft end 80, exposing the clevis 86. Once the rod end 84 clears the shaft end 80, the tip 124 of the stub shaft 118 can be removed from the clevis 86 and the entire end tool 14 discarded. It is not necessary to remove the rod 64 from the handle portion 12 or disconnect the extension 68 from the handle upper end 30.

Reattachment of a fresh end tool 14 is accomplished by reversing the aforementioned sequence of steps. Specifically, a fresh tool 14, preferably sterile and kept separate in its own sealed package (not shown), is placed adjacent to the shaft end 80 and the tip 124 placed into the clevis 86. The handles 17, 18 are spread slightly and the support 88 is threaded into the shaft end 80. In the preferred embodiment, the threaded end 90 of the support 88 includes bosses 126 which are deformed by the threads of the threaded end 80 to prevent the inadvertent unthreading of the end tool 14.

As a result of the design of the end tool 14, rod clevis 84 and shaft 56, the end tool can be threaded onto the shaft end 80 by hand, without tool, such as wrenches, pliers and the like, by a nurse or other operative attendant immediately prior to an operation. This enables the attendant to customize the endoscopic instruments used during a particular operation to suit the desires of a particular surgeon by selecting tools from a variety of shapes and configurations. Consequently, the attendant need only have a relatively few handle portions 12 on hand, each of which can be fitted with a selected one of a variety of different end tools 14, each designed for a specific application and inventoried sterile in separate packages.

After the operation, the end tool 14 can be removed by hand without tools and discarded, along with other biohazardous waste generated during the operation. The bosses 126 are not shaped so that the acts of threading and unthreading of the tool 14 onto the shaft end 80 cannot be done by hand. The handle portions 12 remaining can then be sterilized as follows.

To clean the handle portion 12 of the instrument system 10, the tip 14 is first removed as previously described. Then, the nut 58 is removed from the tube 57 and a cleaning solvent is flushed through the interiors 32, 62 of the housing 24 and shaft 56 so that the solvent exits the end 80 of the shaft, thereby flushing any debris from the shaft. However, it should be noted that the connection of the tip 14 with the shaft end 80 minimizes the entry of contaminants within the interior 62, since the only openings are the seam between the shaft end and support 88 and the passage 120 and stub shaft 118.

Figure 6:
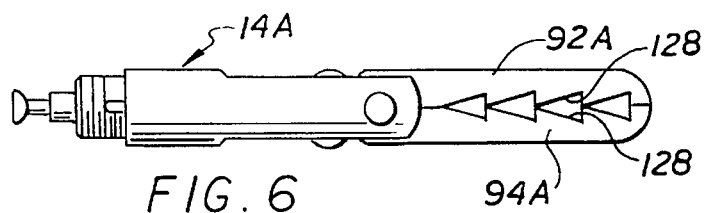
FIG. 6 is a side elevation of a gripper end tool of the present invention.
Figure 7:
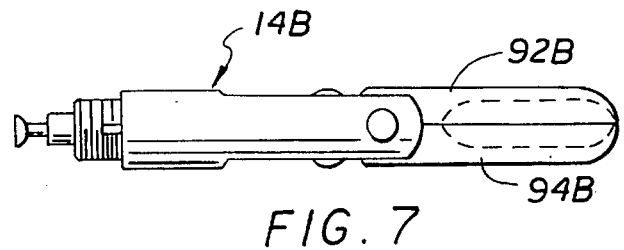
FIG. 7 is a side elevation of a biopsy end tool of the present invention.
Figure 8:
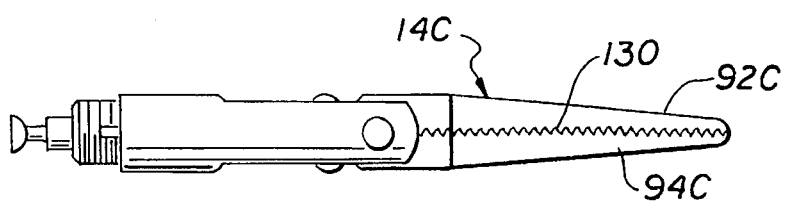
FIG. 8 is a side elevation of a dissector end tool of the present invention.

FIGS. 6, 7 and 8 show alternate embodiments of the end tool 14A, 14B, 14C, each designed to perform a specialized function and forming a component of the system 10. In 14A, the jaws 92A, 94A include rear-facing sawtooth edges 128 such that the tip 14A forms an alligator grasper. In FIG. 7, the end tool 14B includes jaws 92B, 94B which are shaped to form a biopsy. In FIG. 8, the end tool 14C includes jaws 92C, 94C having sawtooth edges 130 to form a dissector.

While the form of apparatus herein described constitute a preferred embodiment of the invention, it is to be understood that the invention is not limited to this precise form of apparatus, and that changes may be made therein without departing from the scope of the invention.

What is claimed is:

1. An endoscopic instrument system comprising:
   an instrument including a handle portion having means for gripping said instrument, means forming a shaft extending from gripping means and means for actuating said instrument, said actuating means including a clevis; and
   an instrument end tool, said end tool having means for mounting said end tool on an end of said shaft and including an enlarged end which is shaped to be seated in said clevis, whereby an attached one of said end tools is operable by said actuating means, said mounting means and said enlarged end being shaped such that said end tool is attachable to said shaft end and removable therefrom by hand without tools.

2. The system of claim 1 further comprising a plurality of said end tools, said end tools having different configurations for performing different tasks.

3. The system of claim 2 wherein said actuating means extends through said shaft from said gripping means to an attached one of said end tools.

4. The system of claim 3 wherein said end tools include scissors.

5. The system of claim 3 wherein said end tools are connectable to said shaft end by a threaded engagement.

6. The system of claim 5 wherein said actuating means includes a rod extending from said gripping means to one of said end tools mounted on said shaft end.

7. The system of claim 6 wherein each of said end tools includes means for engaging said rod.

8. The system of claim 7 wherein each of said end tools includes link means terminating in said enlarged end, and said actuating means includes means for releasably engaging said enlarged end.

9. The system of claim 8 wherein said shaft is rotatably mounted on said gripping means.

10. The system of claim 8 wherein said shaft is removable from said gripping means.

11. The system of claim 8 wherein each of said end tools includes a support attachable to said shaft end and receiving said link means, a first element pivotally attached to said support and to said link means and a second element attached to said support, whereby movement of said link means in response to movement of said actuating means causes said first element to pivot relative to said support and to said second element.

12. The system of claim 11 wherein said link means includes a stub rod having said enlarged end and being slidably received in said support, and a first link element interconnecting said stub rod and said first element, whereby sliding movement of said stub rod is transmitted through said link element to pivot said first element.

13. The system of claim 12 wherein said second element is pivotally attached to said support, and said link means includes a second link element interconnecting said stub rod and said second element, whereby said sliding movement of said stub rod causes said first and second elements to pivot relative to each other in a scissors movement.

14. The system of claim 13 wherein said first and second elements comprise first and second jaws, respectively, of a scissors.

15. The system of claim 1 wherein said gripping means includes port means for flushing said shaft.

16. The system of claim 15 wherein said port means includes a stub tube threaded into said gripping means communicating with said shaft.

17. For use with an endoscopic instrument of a type having a handle portion including means for gripping said instrument, means forming an elongate shaft extending from said gripping means and having an open end opposite said gripping means and means for actuating said instrument, a disposable end tool comprising:
   means forming a pair of jaws; and
   means for supporting said jaw means such that said jaw means move relative to each other, said supporting means being shaped for attachment to and detachment from an associated shaft end by hand without tools, and said support means including an inner end adapted to mount on said shaft end, and
   a stub shaft mounted within said support,
   such that said actuating means moves said jaw means through said stub shaft and said end tool is replaceably removable from said shaft end without damage to said shaft end.

18. The end tool of claim 17 wherein said inner end includes a threaded portion shaped to thread into said shaft end.

19. The end tool of claim 17 wherein said jaw means includes a stub shaft slidably mounted in said support means and adapted to engage said actuating means.

20. The end tool of claim 19 wherein said stub shaft includes an end protruding from said inner end and shaped to engage said actuating means.

21. The end tool of claim 20 wherein said jaw means includes first and second jaws, said jaws being pivotally attached to said support means.

22. The end tool of claim 21 wherein said jaw means includes first and second links interconnecting said first and second jaws, respectively, with said stub shaft, whereby reciprocating movement of said stub shaft relative to said support means in response to said actuating means causes said jaws to pivot relative to each other.

23. The end tool of claim 17 wherein said support means is made of a plastic material.

24. The end toll of claim 23 wherein said plastic material is selected from the group consisting of: a glass filled polyetherimide, a glass filled polyetheretheketone and a glass filled polyethersulfone.

25. The end tool of claim 21 wherein said jaws form a scissors.

26. For use with an endoscopic instrument of a type having a handle portion including means for gripping said instrument, means forming an elongate shaft extending from said gripping means and having a threaded open end opposite said gripping means, rod means for actuating said instrument, said rod means being mounted within said shaft for slidable movement by said gripping means and having a clevis end adjacent said shaft end, a disposable end tool comprising:

a support having a threaded inner end shaped to be threaded into and threaded out of said shaft end by hand without tools;

a stub shaft mounted within said support for reciprocal movement and having an enlarged end protruding from said inner end shaped to releasably engage an associated clevis end;

first and second links pivotally attached to said stub shaft within said support;

first and second jaws pivotally mounted on said support to effect a scissors movement, said first and second jaws being pivotally connected to said first and second links, respectively, whereby reciprocating movement of associated rod means reciprocates said stub shaft and effects said scissors movement of said jaws.

27. A method of providing an instrument system for endoscopic surgery comprising:

selecting an endoscopic instrument of a type having a handle portion and a shaft adapted to receive a disposable end tool;

selecting a disposable end tool having a predetermined tool configuration; and attaching said end tool to said shaft by hand without tools such that said end tool is actuatable by said handle portion.

28. The method of claim 27 further comprising the step of, subsequent to said attaching step, performing said surgery.

29. The method of claim 28 further comprising the step of, subsequent to said performing step, detaching said end tool from said instrument by hand without tools.

30. A method of performing endoscopic surgery comprising:

selecting an endoscopic instrument of a type having a handle portion and a shaft adapted to receive a disposable end tool;

attaching a disposable end tool having a predetermined tool configuration;

performing a surgical procedure using said instrument and said end tool.

31. The method of claim 30 further comprising the step of disposing of said end tool subsequent to said detaching step.

32. A surgical instrument for laparoscopic procedures comprising:

a distal portion, an intermediate portion, and a proximal portion;

the distal portion comprising first and second pivotally connected arms connected at one end to a lever means, the first and second pivotally connected arms also having unattached ends with opposing faces;

the intermediate portion comprising an actuating rod having a distal end and a proximal end and a rigid tube having a distal tip and a proximal tip, the actuating rod being slidably located inside the rigid tube;

the proximal portion comprising first and second handle means;

the distal end of the actuating rod being connected to the lever means;

the first handle means immovably connected to the rigid tube;

the second handle means pivotally coupled to the proximal end of the actuating rod;

the first handle means pivotally connected to the second handle means;

the first and second handle means operable to remotely cause the unattached ends of the first and second pivotally connected arms to move angularly toward and away from each other into closed and opened positions; and the surgical instrument further comprising a rigid tubing extension having a distal tip and a proximal tip, the proximal tip of said rigid tubing extension being removably engaged to the distal tip of the rigid tube; and an actuating rod extension for connecting the distal end of the actuating rod to the lever means, the actuating rod extension having a proximal tip and a distal tip;

the distal end of the actuating rod being removably engaged with the proximal tip of the actuating rod extension.

* * * * *